United States Patent [19]

Shin

[11] Patent Number: 4,777,035

[45] Date of Patent: Oct. 11, 1988

[54] ANTIPERSPIRANT COMPOSITION AND PROCESS

[75] Inventor: Chung T. Shin, Livingston, N.J.

[73] Assignee: Bristol-Myers Company, New York, N.Y.

[21] Appl. No.: 798,773

[22] Filed: Nov. 15, 1985

[51] Int. Cl.[4] .................... A61K 7/32; A61K 7/34; A61K 7/38

[52] U.S. Cl. ................................. 424/66; 424/68

[58] Field of Search ........................ 424/66, 68

[56] References Cited

U.S. PATENT DOCUMENTS

| | | | |
|---|---|---|---|
| 3,710,510 | 1/1973 | Tully et al. | 47/58 |
| 4,078,051 | 3/1978 | Promot et al. | 424/35 |
| 4,080,438 | 3/1978 | Promot et al. | 424/35 |
| 4,102,703 | 7/1978 | Tully | 106/207.14 |
| 4,151,272 | 4/1979 | Geary et al. | 424/68 |
| 4,183,911 | 1/1980 | Smithies et al. | 424/36 |
| 4,268,411 | 5/1981 | Iwata et al. | 252/316 |
| 4,278,206 | 7/1981 | Prussin | 239/327 |
| 4,364,515 | 12/1982 | Prussin | 239/8 |
| 4,369,173 | 1/1983 | Gausland et al. | 424/35 |
| 4,398,954 | 8/1983 | Stolfo | 106/21 |
| 4,605,554 | 8/1986 | Prussin et al. | 424/66 |
| 4,680,173 | 7/1987 | Burger | 424/47 |

FOREIGN PATENT DOCUMENTS

| | | | |
|---|---|---|---|
| 895610 | 7/1983 | Belgium | 424/47 |
| 2532191 | 3/1984 | France | 424/59 |
| WO80/00394 | 8/1980 | PCT Int'l Appl. | 424/47 |
| GB2018590A | 10/1979 | United Kingdom | 424/47 |
| 2078543 | 1/1982 | United Kingdom | 514/937 |
| 2079179 | 1/1982 | United Kingdom | 514/937 |

OTHER PUBLICATIONS

D. Schutte, et al,. (3,393,155), Jan. 16, 1968, Predominately Aqueous Compositions, etc.

Primary Examiner—Dale R. Ore
Attorney, Agent, or Firm—Morton S. Simon

[57] ABSTRACT

An antiperspirant composition for roll-on application, which feels dry upon application, is prepared by encapsulating a relatively large amount of water onto a specific kind of a hydrophobic silica, and then suspending the water-loaded silica into an anhydrous liquid vehicle which has a particular antiperspirant material suspended therein.

12 Claims, No Drawings

ANTIPERSPIRANT COMPOSITION AND PROCESS

This invention relates to a liquid antiperspirant composition suitable for application from the so-called roll-on dispensers. More particularly it concerns a modified suspension type liquid antiperspirant composition of the above identified type which has the advantages of the non-aqueous suspension type products but not the expense of such products.

For a long time the conventional antiperspirant roll-on type compositions took the form of aqueous oil-in-wateer emulsions in which the active antiperspirant material was in solution in the aqueous phase. These products exhibited a number of disadvantageous characteristics in that when applied they gave a "wet" and "tacky" feel. In an effort to avoid these negative characteristics non-aqueous suspension roll-on products were developed which were characterized by the fact that the dry active antiperspirant material in particulate form was suspended in a non-aqueous oily carrier usually with the aid of a suspending agent. Popular oily vehicles for this purpose were the volatile silicones. These products were improvements over the older aqueous oil-in-water emulsion type products. However, they are inclined to be expensive because of the high cost of goods for the raw materials.

In an effort to reduce the cost of goods an effort was made to substitute a quantity of water for the more expensive oily vehicles in the anhydrous suspension type product. It was found, however, that if more than 5% of water was added to an anhydrous suspension type roll-on product that the stability of this suspension is compromised.

SUMMARY OF INVENTION

It has now been found that as much as 30% by weight of water may be incorporated in an anhydrous antiperspirant suspension type roll-on product without encountering a stability problem. This is accomplished by also suspending in the anhydrous antiperspirant suspension type composition an aqueous component encapsulated in a particular class of hydrophobic silicas defined in more detail below. This system is not only stable but it is non-tacky and dry feeling on application. Organoleptically it is similar to an anhydrous suspension roll-on system, and yet has a significantly lower cost of goods.

PRIOR ART

Belgian Pat. No. 895,610 issued to the assignees of the present application discloses an oily liquid/polar liquid suspension product system and a method for its preparation. In the Belgian patent droplets of a polar liquid such as an aqueous solution of active antiperspirant material is encapsulated in a hydrophobic silica which is then suspended in an oily liquid vehicle. In the Belgian invention all of the active antiperspirant material is pressent in the encapsulated aqueous phase. In contrast to this, in the present invention, essentially all of the antiperspirant material is external to the encapsulated aqueous material and is suspended in the outside oily vehicle.

U.K. Patent Application GB 201 8590 A teaches the preparation of an antiperspirant suspension type composition in which active antiperspirant material is suspended in a volatile silicone vehicle using Bentone or Cab-O-Sil (fumed silica) as suspending agent. These products are also quite different structurally from that of the present invention. Furthermore the suspending agents employed in the U.K. patent is also quite distinct from the hydrophobic silica employed in this invention.

U.S. Pat. No. 3,393,155 to Schutte et al is of interest in showing the encapsulation of water in a hydrophobic, pyrogenic silica to form a dry power. There is, however, no suggestion for the incorporation of this material in an antiperspirant suspension type system.

Prussin International Patent application No. 80/02293 and U.S. Pat. No. 4,364,515 describe a water-in-air emulsion or suspension containing a dispersible material formed of small droplets of aqueous liquid with an interfacial barrier of very fine hydrophobic metal oxide particles such as silane modified silica. Active ingredients such as antiperspirants may be added to either the aqueous liquid phase or to the powder phase as long as they do not destabilize the stability of the suspension. The resulting powder when subjected to shear such as during passage through an orifice is converted into a cream.

DESCRIPTION OF INVENTION

As indicated above it is a feature of the present invention to incorporate in an anhydrous antiperspirant suspension type composition a hydrophobic silica encapsulated aqueous component. The anhydrous antiperspirant suspension type component of the composition of this invention can be of the conventional type known to those skilled in this art. The aqueous component may simply be water or aqueous solutions containing any of a variety of materials in solution including active antiperspirant materials encapsulated in said hydrophobic silica. However, in the latter case the lion's share of active antiperspirant material will still be provided by the particles of active antiperspirant material that are suspended in the anhydrous antiperspirant suspension component. The encapsulated aqueous component may also take the form of an aqueous emulsion e.g. the water-in-oil type encapsulated in said hydrophobic silica. The water phase in this emulsion may also have dissolved therein a variety of water soluable materials including active antiperspirant materials.

The hydrophobic silicas employed in this invention are also pyrogenic silicas but are distinguished from the generally conventional pyrogenic silica (e.g. Cab-O-Sil) by its mode of preparation which gives it its particular hydrophobic character. These hydrophobic products are prepared by reacting the conventional pyrogenic silica with an organosilane such as halo alkyl silanes (e.g. dimethyl dichlorosilane) under conditions which causes a chemical reaction to occur with a substantial portion of the hydroxyl groups on the surface of the pyrogenic silica. This gives a new surface structure on the outer or exposed portions of the silica which is largely composed of hydrocarbon groups.

The preparation of hydrophobic silicas that are useful for the purposes of the present invention are described in U.S. Pat. No. 3,393,155 col. 2, line 25 to col. 3, line 18 and in the Example, col. 3, line 70 to col. 4, line 6 which is incorporated herein by way of reference. As pointed out therein, the pyrogenic silicas that may be employed in preparing the hydrophobic silicas that can be used herein are those having a surface area of at least about 100 sq. meters per gram and mean equivalent particle diameters of less than 50 millimicrons per gram. In order to provide a sufficiently hydrophobic surface on said silicas for the purpose of this invention, it is merely necessary to attach thereto in suitable concentration chemical complexes bearing hydrocarbon or similar organo groups. The molar area concentration of such complexes required per unit of surface area will depend somewhat on the number and size of the organo groups therein. However, for the organo silane complexes of primary interest, which carry from 1 to 3 organo groups mostly of smaller size (e.g. usually not over 7 carbon atoms per group), the concentrations of the attached chemical complexes should be in the range of about 0.2 millimoles or more per 100 sq. meters of surface area of the silica. For the preferred silicas having BET surface areas of at least about 150 sq. meters per gram, the carbon content after surface treatment to provide a suitable hydrophobic character will usually be about 1% by weight or more.

A number of hydrophobic silicas sold commercially are employable in the present invention. These include "Aerosil R 972" or "Silica R 972" (Degussa Inc.), "Tullanox 500" (Tulco Inc.), "Silanox" (Cabot Corp.), CAB-O-Sil N 70-TS etc. A material of choice is Silica R 972 currently marketed by Degussa Inc.

The compositions of this invention may be prepared in a variety of ways. In one such preferred procedure the encapsulated aqueous component (as water, aqueous solution, water-in-oil emulsion) and the anhydrous antiperspirant suspension component are made separately and then mixed together. When the encapsulated aqueous component is formed by encapsulating a water-in-oil or aqueous solution-in-oil emulsion in said hydrophobic silica on a microscopic scale the product appears as a wet gel which may be readily dispersed in the anhydrous antiperspirant suspension components of this invention.

Any of a variety of oily materials may be utilized in forming the oil-in-water or aqueous solution-in-oil emulsions that are to be encapsulated in accordance with the present invention. By way of example volatile emollients (cyclomethicones) and nonvolatile emollients (dimethicone, fatty esters, etc.) or their combinations can be mentioned.

The relative quantities of the respective materials used in preparing the encapsulated aqueous component employed in this invention can be important in determining the stability and the character of the finished product. Since these are related to the finished product it may be best to define these quantities in terms of the total composition. The general and preferred ranges for these materials are given in Table 1 below.

TABLE I

| | ENCAPSULATED WATER COMPONENT | |
|---|---|---|
| | % by Wt. base of total wt. of finished product | |
| Material | General Range | Preferred Range |
| Pyrogenic Silica | about 0.1% to about 1.6% | about 0.2% to about 1.0% |
| Water | about 5% to about 50% | about 10% to about 30% |
| Oil | about 20% to about 60% | about 30% to about 50% |

It may also be advantageous to add auxilliary aids to the encapsulated aqueous component. These may be used to facilitate its preparation, to increase its stability, to act as a preservative, to improve its organoleptic properties etc. Illustrative of the auxilliary that can be employed are Germaben II (Preservative), EDTA Na$_2$ (chelating agents), glycols (humectants), water soluable or dispersible thickening agents (Veegum, Methocel, Klucel, etc.).

As indicated above in preparing the finished product of this invention the encapsulated aqueous component described above is dispersed in a liquid anhydrous antiperspirant suspension component. Compositions of this type are known in this art and comprise essentially particulate antiperspirant active material distributed in a anhydrous oily liquid vehicle. A variety of such liquids are known in this art which are useful for this purpose. These will advantageously be volatile oily organic liquids many of which have been used in this art in making anhydrous suspension type antiperspirant products. By way of example mention may be made of various Cyclomethicones and mixtures thereof. In the preferred form of this invention the non-aqueous vehicle will be constituted primarily by one or more volatile silicones (e.g. one or more Cyclomethicones, such as Cyclomethicones 7158 or Cyclomethicones 7207 or their combinations).

A number of volatile silicones are available on the market which may be employed for the present purposes. These included such materials as Volatile Silicone 7158 (Union Carbide), Siloxane F-222 (SWS SILICONES), Dow Corning Q2-1201 Fluid, Silicone Fluid SF-1202 (General Electric), Volatile Silicone 7207 (Union Carbide), Siloxane 03314 (General Electric) etc. Additional examples of Cyclomethicones that may be employed are given in the CTFA Cosmetic Ingredient Dictionary, Third edition, 1982 (published by the Cosmetic, Toiletry and Fragrance Association, Inc., Washington, D.C.) at p. 60, which is incorporated herein by way of reference. One or more of the aforesaid Cyclomethicones may be used alone or in combination with each other.

Cyclomethicones are cyclic dimethyl polysiloxanes. They conform to the following general formula:

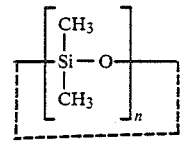

wherein n has an average value of between 3 and 6.

The quantity of anhydrous oily liquid vehicles usd in the anhydrous antiperspirant component of this invention may vary somewhat. Generally, this will constitute between about 20% to about 60% by weight based on the total weight of the composition with preferred range being from about 30% to about 50% on the same weight basis.

In the anhydrous, antiperspirant suspension component of this invention the active antiperspirant material is suspended in the non-aqueous vehicle. This material is employed in a dry particulate form as for example as powders, granules, crystals etc. that is intimately distributed in the vehicle. The particle sizes of these materials can vary widely but usually they will be in the range of from about 5 to 70 microns in size.

Any of the variety antiperspirant material well known to those skilled in the art can be used for the present purposes. These include such materials as aluminum chlorohydrate, aluminum sesquichlorohydrate, aluminum zirconium polychlorohydrate glycine, or their combinations.

The aluminum zirconium polychlorohydrate complexes that can be incorporated in the composition of the present invention can be described by the general formula:

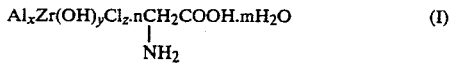

wherein:
(a) x is a number from 2 to 10;
(b) Z is a number from 3 to 8;
(c) y equal (3x+4)-Z;
(d) the sum of y+Z is a number from 10 to 34;
(e) m is a number from 0 to 12;
(f) n is a number from 0 to 3 y ordinarily will have a value of from about 5 to about 29.

As will be clear from the above formula, the glycine can be bound in the complex or it can be absent. The presence or absence of the glycine in the complex will determine the amount of unbound glycine or other buffer that may be incorporated in the composition to increase the pH to a level of from about 2.5 to about 4.5 or the preferred pH of from about 2.8 to about 3.8.

A number of aluminum zirconium polychlorohydrate complexes are known in the prior art which are useful for the present purposes. By way of example, the following can be mentioned along with their empirical formulas: aluminum zirconium tetrachlorohydrate ($Al_4Zr(OH)_{12}Cl_4$); aluminum zirconium tetrachlorohydrate glycine (sold under the name of Wickenol #E-369) ($Al_4Zr(OH)_{12}Cl_4 \cdot NH_2CH_2COOH$); aluminum zirconium trichlorohydrate ($Al_4Zr(OH)_{13}Cl_3$); aluminum zirconium trichlorohydrate glycine ($Al_4Zr(OH)_{13}Cl_3 \cdot NH_2CH_2COOH$); aluminum zirconium pentachlorohydrate ($Al_{10}Zr(OH)_{29}Cl_5$); aluminum zirconium pentachlorohydrate glycine ($Al_{10}Zr(OH)_{29}Cl_5 \cdot NH_2CH_2COOH$); aluminum zirconium octachlorohydrate ($Al_6Zr(OH)_{14}Cl_8$); aluminum zirconium octachlorohydrate glycine ($Al_6Zr(OH)_{14}Cl_8 \cdot NH_2CH_2COOH$).

The OTC Panel on antiperspirants of the Food and Drug Administration has adopted certain nomenclature and specifications for various aluminum zirconium polychlorohydrates that are useful in the present invention. These are set out in Table A below:

TABLE A

| Panel Adopted Nomenclature | Metal-Halide Ratio Range | Al/Zr Ratio Range |
| --- | --- | --- |
| Aluminum zirconium trichlorohydrate | 2.1 down to but not including 1.5:1 | 2.0 up to but not including 6.0:1 |
| Aluminum zirconium tetrachlorohydrate | 1.5 down to and including 0.9:1 | 2.0 up to but not including 6.0:1 |
| Aluminum zirconium pentachlorohydrate | 2.1 down to but not including 1.5:1 | 6.0 up to and including 10.0:1 |
| Aluminum zirconium octachlorohydrate | 1.5 down to and including 0.9:1 | 6.0 up to and including 10.0:1 |

Exceptionally good results are obtained with aluminum zirconium tetrachlorohydrex glycine (CTFA nomenclature Aluminum zirconium tetrachlorohydrex gly) complexes employed in dry powdered form. This material will have a particle size of about 5 to about 70 microns. These materials are available in the trade under the trade names WICKENOL-369 (Wickhen), REZAL 36 GP (Reheis) and WESTCHLOR ZR 35 B (Westwood).

The quantity of active antiperspirant material usable in this invention can vary depending upon the nature of the other ingredients selected and the results desired. Usually, this will comprise from about 10% to about 30% by weight based on the total weight of the composition with the best results being obtained when the active antiperspirant constitute from about 15% to about 25% on the same weight bases.

It is often highly desirable to also incorporate in the anhydrous antiperspirant suspension component of this invention a nonvolatile liquid emollient. This will add to the elegance of the product giving it enhanced organoleptic properties. A variety of non-polar emollients may be used for the purposes of this invention. By way of example, mention may be made of fatty acid monoesters (isopropyl myristate), fatty acid diesters (Neobee M-20, dibutyl phthalate), branched fatty acid esters (2-ethyl hexyl pelargonate, 2-ethyl hexyl palmitate, 2-ethyl hexyl stearate, etc.), polyoxypropylene fatty ($C_4$–$C_{18}$) ethers (Witconol APS, Fluid AP), polysiloxanes (polydimethyl-siloxanes), fatty alcohols (hexadecyl alcohol), etc. Suitable non-polar emollients that can be used herein are described in U.S. Pat. No. 3,968,203 column 3, lines 48 to 63. These include such materials as a nonvolatile linear polydimethylsiloxanes.

Of special interest are the Dimethicones having a viscosity of from about 100 cs to about 1,000 cs (and preferably about 350 cs). These materials are described in the CTFA Cosmetic Ingredient Dictionary, Third edition, 1982 of page 83, and conform to the formula

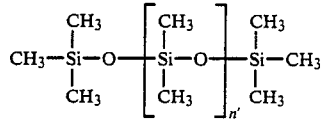

wherein n' is a cardinal number.

These are available commercially as Silicone Fluid SF18 (General Electric), Silicone Fluid SWS-101 (SWS Silicones), Silicone Fluid 200 (Dow Corning).

The quantity of nonvolatile liquid emollient that will be contained in the anhydrous antiperspirant suspension component is variable. Usually this will constitute between about 2% to about 15% by weight based on the total weight of the composition. The preferred range being from about 3% to about 10% on the same weight basis.

In addition to the components described above the compositions of the present invention may, optionally contain a number of other ingredients. Thus it might contain processing aids, odor masking agents, perfumes, coloring agents, perfumes, talc, Dry Flo, antibacterial agents, preservatives, etc. A polyethylene powder, as for example, a product sold under the trade name Polymist B-6 is useful as a processing aid. As an odor masking aid ethylene brassylate (sold under the trade name Ethylene Brassylate, Musk T-Takasago) has been used with advantage.

The following examples are given to further illustrate the present invention. It is to be understood, however, that the invention is not limited thereto.

EXAMPLE 1

FORMULA No. 2428

| Ingredients | % By Weight |
|---|---|
| 1. Aluminum Zirconium Tetrachlorohydrex-Gly Solution (35% aqu.) (Rezal 36G Solution - Reheis) | 40.00 |
| 2. Silica R-972 (Aerosil R-972 - Degussa) | 0.91 |
| 3. Cyclomethicone SF 1202 (G.E.) | 37.28 |
| 4. Cyclomethicone 03314 (SWS) | 7.48 |
| 5. Dimethicone 350 c.s. (GE Silicone SF 18 [359]) | 4.39 |
| 6. Dimethyldioctadecyl Ammonium Hectorite (Bentone 38, N L Industries) | 0.48 |
| 7. Propylene Carbonate (Texaco) | 0.16 |
| 8. Colloidal Silicon Dioxide, M-5 (Cab-O-Sil M-5-Cabot) | 0.06 |
| 9. Polyethylene B-6, 6 Micron (Polymist B-6 - Allied Chemical) | 1.59 |
| 10. Aluminum Zirconium Tetrachlorohydrex-Gly Powder W-369 (Wickenol 369 - Wickhen Products) | 7.65 |
| | 100.00 |

The product is an off-white opaque suspension and has a Brookfield RVT viscosity of (Spindle #4, 20 RPM 15 sec.)
Initial: 2500 ± 1500 cps
Overnight: 2500 ± 1500 cps Note: Procedure A. Gel Preparation The dimethyldioctadecyl ammonium hectorite is dispersed in 4.13% of the formula weight of cyclomethicone SF 1202. It is mixed until homogeneous. Then the formula weight of propylene carbonate is added and mixed until homogeneous. Homogenize with a Waring blender or any other homogenizer to form a thick gel.

B. Antiperspirant suspension preparation

The resulting gel is transferred into a suitable vessel and the cyclomethicone 03314, 7.09% of the formula weight of cyclomethicone SF 1202, and 3.18% of the formula weight of dimethicone (350 cs) are added to the batch and mixed until homogeneous. Then colloidal silicon dioxide, M-5 is added and mixing is continued until homogeneous. Then the polyethylene, and the aluminum zirconium tetrachlorohydrex-gly powder (W-369) are added and mixed until homogeneous.

C. Antiperspirant Gel Preparation

The Silica R 972 is dispersed in 18.18% of the formula weight of cyclomethicone SF 1202 with a "Lightnin" mixer until homogeneous. The Al/Zr tetrachlorohydrex-gly aqueous solution is added. The remaining cyclomethicone SF 1202 and dimethicone 350 cs are then added and mixed until uniform.

D. Antiperspirant Emulsion Suspension Preparation

Slowly add the step B, antiperspirant suspension to Step C, antiperspirant gel and mix well until homogeneous. If the viscosity is lower than 1000 cps, homogenize the batch to get the proper viscosity (2500±1500 cps).

This product was tested for antiperspirant activity by applying it to the underarm of human subjects. This was found to be as effective as a commercially available antiperspirant roll-on-product.

EXAMPLE 2

FORMULA No. 2439

| Ingredients | % By Weight |
|---|---|
| 1. Water, Deionized | 29.39 |
| 2. Germaben II Solution (Sutton) | 0.25 |
| 3. Cyclomethicone SF 1202 (G.E.) | 31.52 |
| 4. Silica R-972 (Aerosil R-972 - Degussa) | 0.59 |
| 5. Cyclomethicone 03314 (SWS) | 8.23 |
| 6. Dimethyldioctadecyl Ammonium Hectorite (Bentone 38, N L Industries) | 0.53 |
| 7. Propylene Carbonate (Texaco) | 0.17 |
| 8. Dimethicone 350 c.s. (GE Silicone SF 18 [350]) | 3.50 |
| 9. Colloidal Silicon Dioxide, M-5 (Cab-O-Sil M-5-Cabot) | 0.07 |
| 10. Polyethylene B-6, 6 Micron (Polymist B-6 - Allied Chemical) | 1.75 |
| 11. Aluminum Zirconium Tetrachlorohydrex-Gly Powder W-369 (Wickenol 369 - Wickhen Products) | 24.00 |
| | 100.00 |

The resulting material is an off-white opaque suspension and has a Brookfield RVT viscosity of (Spindle #4, 20 RPM, 15 sec.)
Initial: 4500 ± 1700 cps
Overnight: 4500 ± 1700 cps This product was tested for antiperspirant activity by applying it to the underarm of human subjects. This was also found to be as effective as a commercially available antiperspirant roll-on product.

EXAMPLE 3

FORMULA No. 2440

| Ingredients | % By Weight |
|---|---|
| 1. Water, Deionized | 29.39 |
| 2. Germaben II Solution (Sutton) | 0.25 |
| 3. Cyclomethicone SF 1202 (G.E.) | 31.52 |
| 4. Silica R-972 (Aerosil R-972 - Degussa) | 0.59 |
| 5. Cyclomethicone 03314 (SWS) | 8.23 |
| 6. Dimethyldioctadecyl Ammonium Hectorite (Bentone 38, N L Industries) | 0.53 |
| 7. Propylene Carbonate (Texaco) | 0.17 |
| 8. Dimethicone 350 c.s. (GE Silicone SF 18 [350]) | 3.50 |
| 9. Colloidal Silicon Dioxide, M-5 (Cab-O-Sil M-5-Cabot) | 0.07 |
| 10. Polyethylene B-6, 6 Micron (Polymist B-6 - Allied Chemical) | 1.75 |
| 11. Aluminum Chlorohydrate Impalpable Powder (Micro Dry - Reheis) | 24.00 |
| | 100.00 |

The product is an off-white opaque suspension and has a Brookfield RVT viscosity of (Spindle #4, 20 RPM, 15 sec.)
Initial: 5000 ± 2000 cps Overnight: 5000 ± 2000 cps This product was tested for antiperspirant activity by applying it to the underarm of human subjects. This was found to be as effective as a commercially available antiperspirant roll-on product.

EXAMPLE 4

FORMULA 2447

| Ingredients | % By Weight |
|---|---|
| 1. Water, Deionized | 29.38 |
| 2. Germaben II Solution (Sutton) | 0.25 |
| 3. Cyclomethicone SF 1202 (G.E.) | 31.51 |
| 4. Silica R-972 (Aerosil R-972 - Degussa) | 0.59 |
| 5. Cyclomethicone 03314 (SWS) | 8.23 |
| 6. Dimethyldioctadecyl Ammonium Hectorite (Bentone 38, N L Industries) | 0.53 |
| 7. Propylene Carbonate (Texaco) | 0.17 |
| 8. Dimethicone 350 c.s. (GE Silicone SF 18 [350]) | 3.50 |
| 9. Colloidal Silicon Dioxide, M-5 (Cab-O-Sil M-5-Cabot) | 0.07 |
| 10. Polyethylene B-6, 6 Micron (Polymist B-6 - Allied Chemical) | 1.75 |

FORMULA 2447 -continued

| Ingredients | % By Weight |
|---|---|
| 11. Aluminum Chlorohydrate Impalpable Powder (Micro Dry - Reheis) | 24.00 |
| 12. Ethylene Brassylate (Takasago) | 0.02 |
| | 100.00 |

The product is an off-white opaque suspension and has a Brookfield RVT viscosity of (Spindle #4, 20 RPM, 15 sec.)
Initial: 2250 ± 750 cps
Overnight: 2250 ± 750 cps This formula is similar to Formula No. 2440 except ethylene brassylate (masking agent) is used. It is understood that addition of perfume does not interfere with antiperspirant activity.

EXAMPLE 5

FORMULA No. 2448

| Ingredients | % By Weight |
|---|---|
| 1. Water, Deionized | 29.38 |
| 2. Germaben II Solution (Sutton) | 0.25 |
| 3. Cyclomethicone SF 1202 (G.E.) | 31.51 |
| 4. Silica R-972 (Aerosil R-972 - Degussa) | 0.59 |
| 5. Cyclomethicone 03314 (SWS) | 8.23 |
| 6. Dimethyldioctadecyl Ammonium Hectorite (Bentone 38, N L Industries) | 0.53 |
| 7. Propylene Carbonate (Texaco) | 0.17 |
| 8. Dimethicone 350 c.s. (GE Silicone SF 18 [350]) | 3.50 |
| 9. Colloidal Silicon Dioxide, M-5 (Cab-O-Sil M-5-Cabot) | 0.07 |
| 10. Polyethylene B-6, 6 Micron (Polymist B-6 - Allied Chemical) | 1.75 |
| 11. Aluminum Zirconium Tetrachlorohydrex-Gly Powder W-369 | 24.00 |
| 12. Ethylene Brassylate (Takasago) | 0.02 |
| | 100.00 |

The product is an off-white opaque suspension and has a Brookfield RVT viscosity of (Spindle #4, 20 RPM, 15 sec.)
Initial: 2500 ± 500 cps
Overnight: 2250 ± 750 cps This formula is similar to Formula No. 2439 except for addition of ethylene brassylate (masking agent). It is believed that addition of perfume does not interfere with antiperspirant activity.

EXAMPLE 6

FORMULA No. 2471

| Ingredients | % By Weight |
|---|---|
| 1. Water, Deionized | 28.05 |
| 2. Germaben II Solution (Sutton) | 0.24 |
| 3. Cyclomethicone SF 1202 (G.E.) | 30.30 |
| 4. Silica R-972 (Aerosil R-972 - Degussa) | 0.28 |
| 5. Cyclomethicone 03314 (SWS) | 7.45 |
| 6. Dimethyldioctadecyl Ammonium Hectorite (Bentone 38, N L Industries) | 0.53 |
| 7. Propylene Carbonate (Texaco) | 0.17 |
| 8. Dimethicone 350 c.s. (GE Silicone SF 18 [350]) | 5.00 |
| 9. Colloidal Silicon Dioxide, M-5 (Cab-O-Sil M-5-Cabot) | 0.07 |
| 10. Polyethylene B-6, 6 Micron (Polymist B-6 - Allied Chemical) | 1.75 |
| 11. Aluminum Zirconium Tetrachlorohydrex-Gly Powder W-369 (Wickenol 369 - Wickhen Products) | 24.00 |
| 12. PPG-1 Ceteth-3 Acetate (Hetester PCA-Heterene Chemical) | 2.00 |
| 13. Butylated Hydroxytoluene (Ionol CP-Shell) | 0.05 |
| 14. Ethylene Brassylate (Takasago) | 0.02 |
| 15. Disodium Edetate Dihydrate (Disodium Edetate - Ciba Geigy) | 0.09 |
| | 100.00 |

The product is an off-white opaque suspension and has a Brookfield RVT viscosity of (Spindle #4, 20 RPM, 15 sec.)
Initial: 1000 ± 250 cps
Overnight: 1150 ± 350 cps

EXAMPLE 7

FORMULA No. 2474

| Ingredients | % By Weight |
|---|---|
| 1. Water, Deionized | 27.94 |
| 2. Germaben II Solution (Sutton) | 0.24 |
| 3. Cyclomethicone 7158 (U.C.) | 30.23 |
| 4. Silica R-972 (Aerosil R-972 - Degussa) | 0.28 |
| 5. Cyclomethicone 03314 (SWS) | 7.45 |
| 6. Dimethyldioctadecyl Ammonium Hectorite (Bentone 38, N L Industries) | 0.53 |
| 7. Propylene Carbonate (Texaco) | 0.17 |
| 8. Dimethicone 350 c.s. (GE Silicone SF 18 [350]) | 5.00 |
| 9. Colloidal Silicon Dioxide, M-5 (Cab-O-Sil M-5-Cabot) | 0.07 |
| 10. Polyethylene B-6, 6 Micron (Polymist B-6 - Allied Chemical) | 1.75 |
| 11. Aluminum Zirconium Tetrachlorohydrex-Gly Powder W-369 (Wickenol 369 - Wickhen Products) | 24.00 |
| 12. PPG-1 Ceteth-3 Acetate (Hetester PCA-Heterene Chemical) | 2.00 |
| 13. Butylated Hydroxytoluene (Ionol CP-Shell) | 0.05 |
| 14. Perfume 3085-AG MOD (IFF) | 0.20 |
| 15. Disodium Edetate Dihydrate (Disodium Edetate - Ciba Geigy) | 0.09 |
| | 100.00 |

The product is an off-white opaque suspension and has a Brookfield RVT viscosity of (Spindle #4, 20 RPM, 15 sec.)
Initial: 1000 ± 250 cps
Overnight: 1150 ± 350 cps

What is claimed is:

1. A stable liquid roll-on antiperspirant composition having a non-tacky dry feeling on application comprising an encapsulated aqueous component and an anhydrous antiperspirant suspension component,
   (a) said encapsulated aqueous component comprising droplets of an aqueous system encapsulated in a pyrogenic hydrophobic silica whose surface structure of exposed portions of said silica is largely composed of hydrocarbon groups,
   (b) said anhydrous antiperspirant component comprising an anhydrous oily organic liquid vehicle having suspended therein an antiperspirant effective amount of active antiperspirant material in particulate form,
   (c) said encapsulated aqueous component also being suspended in the anhydrous liquid vehicle of said anhydrous antiperspirant suspension component,
   (d) said anhydrous oily organic liquid vehicle comprising from about 20% to about 60% by weight of one or more volatile silicones based on the total weight of said composition,
   (e) and said composition containing from about 5% to about 50% by weight of water based on the total weight of said composition.

2. The composition according to claim 1, wherein said volatile silicones are pressent at a concentration in the range of from about 30% to about 50% by weight based on the total weight of the composition, the water is present in said composition at a concentration in the range of from about 10% to about 30% by weight based on the total weight of said composition and said pyrogenic hydrophobic silica is present in said composition at a concentration in the range of from about 0.1% to about 1.6% by weight based on the total weight of said composition.

3. The composition according to claim 2, wherein said volatile silicones are cyclomethicones.

4. The composition according to claim 1, wherein said hydrophobic pyrogenic silica is prepared by reacting conventional pyrogenic silica with a halo alkyl silane under conditions which cause a chemical reaction to occur with a substantial portion of the hydroxyl groups on the surface of said pyrogenic silica.

5. The composition according to claim 4, wherein said aqueous component is an aqueous oil emulsion.

6. The composition according to claim 5, wherein said aqueous oil emulsion is an aqueous solution-in-oil emulsion.

7. The composition according to claim 6, wherein said aqueous solution of said emulsion also has dissolved therein active antiperspirant material.

8. The composition according to claim 5, wherein said aqueous oil emulsion is a water-in-oil emulsion.

9. The composition according to claim 4, wherein said aqueous component is water.

10. The composition according to claim 4, wherein said aqueous component is an aqueous solution.

11. The composition according to claim 10, wherein said aqueous solution is a solution of an active antiperspirant material.

12. The composition according to claim 1, also containing an emollient distributed in said anhydrous liquid vehicle.

* * * * *